(12) United States Patent
Kleshinski et al.

(10) Patent No.: US 8,758,395 B2
(45) Date of Patent: Jun. 24, 2014

(54) EMBOLIC FILTERING METHOD AND APPARATUS

(75) Inventors: Stephen J. Kleshinski, Scituate, MA (US); Scott M. Russell, San Jose, CA (US)

(73) Assignee: SeptRx, Inc., Quakertown, PA (US)

( * ) Notice: Subject to any disclaimer, the term of this patent is extended or adjusted under 35 U.S.C. 154(b) by 2110 days.

(21) Appl. No.: 11/184,069

(22) Filed: Jul. 19, 2005

(65) Prior Publication Data

US 2006/0009799 A1    Jan. 12, 2006

Related U.S. Application Data

(63) Continuation-in-part of application No. 10/847,909, filed on May 19, 2004, now Pat. No. 7,122,043.

(60) Provisional application No. 60/471,555, filed on May 19, 2003.

(51) Int. Cl.
*A61B 17/08* (2006.01)

(52) U.S. Cl.
USPC ........................................ 606/213; 606/151

(58) Field of Classification Search
USPC .................... 606/151, 187, 158, 213
See application file for complete search history.

(56) References Cited

U.S. PATENT DOCUMENTS

| | | | |
|---|---|---|---|
| 3,656,185 A | 4/1972 | Carpentier |
| 3,874,388 A | 4/1975 | King et al. |
| 3,953,566 A | 4/1976 | Gore |
| 4,007,743 A | 2/1977 | Blake |
| 4,055,861 A | 11/1977 | Carpentier |
| 4,187,390 A | 2/1980 | Gore |
| 4,306,319 A | 12/1981 | Kaster |
| 4,739,759 A | 4/1988 | Rexroth et al. |
| 4,787,899 A | 11/1988 | Lazarus |
| 4,917,089 A | 4/1990 | Sideris |
| 4,921,484 A | 5/1990 | Hillstead |
| 4,957,501 A | 9/1990 | Lahille et al. |

(Continued)

FOREIGN PATENT DOCUMENTS

| | | |
|---|---|---|
| EP | 0448891 | 10/1991 |
| EP | 0541063 | 5/1993 |

(Continued)

OTHER PUBLICATIONS

Rao, P. S., Summary and Comparison of Atrial Septal Defect Closure Devices, *Current Interventional Cardiology Reports*, 2000. 2:367-376.

(Continued)

*Primary Examiner* — Corrine M McDermott
*Assistant Examiner* — Alexander Orkin

(57) ABSTRACT

The present invention relates generally to a device and method for preventing the undesired passage of emboli from a venous blood pool to an arterial blood pool. The invention relates especially to a device and method for treating certain cardiac defects, especially patent foramen ovales and other septal defects, through the use of an embolic filtering device capable of instantaneously deterring the passage of emboli from the moment of implantation. The device consists of a frame, and a braided mesh of sufficient dimensions to prevent passage of emboli through the mesh. The device is preferably composed of shape memory allow, such as nitinol, which conforms to the shape and dimension of the defect to be treated.

12 Claims, 11 Drawing Sheets

(56) References Cited

U.S. PATENT DOCUMENTS

| | | | |
|---|---|---|---|
| 4,991,602 | A | 2/1991 | Amplatz et al. |
| 5,059,193 | A | 10/1991 | Kuslich |
| 5,061,277 | A | 10/1991 | Carpentier et al. |
| 5,067,489 | A | 11/1991 | Lind |
| 5,104,407 | A | 4/1992 | Lam et al. |
| 5,108,420 | A | 4/1992 | Marks |
| 5,171,259 | A | 12/1992 | Inoue |
| 5,192,301 | A | 3/1993 | Kamiya et al. |
| 5,234,458 | A | 8/1993 | Metais |
| 5,284,488 | A | 2/1994 | Sideris |
| 5,324,304 | A | 6/1994 | Rasmussen |
| 5,334,217 | A | 8/1994 | Das |
| 5,342,304 | A | 8/1994 | Tacklind et al. |
| 5,356,432 | A | 10/1994 | Rutkow et al. |
| 5,370,657 | A * | 12/1994 | Irie .................... 606/200 |
| 5,425,744 | A | 6/1995 | Fagan et al. |
| 5,433,727 | A | 7/1995 | Sideris |
| 5,486,193 | A | 1/1996 | Bourne et al. |
| 5,507,811 | A | 4/1996 | Koike et al. |
| 5,569,273 | A | 10/1996 | Titone et al. |
| 5,578,045 | A | 11/1996 | Das |
| 5,593,441 | A | 1/1997 | Lichtenstein et al. |
| 5,601,595 | A | 2/1997 | Smith |
| 5,626,599 | A | 5/1997 | Bourne et al. |
| 5,634,931 | A | 6/1997 | Kugel |
| 5,634,936 | A | 6/1997 | Linden et al. |
| 5,649,950 | A | 7/1997 | Bourne et al. |
| 5,669,933 | A * | 9/1997 | Simon et al. .................... 600/200 |
| 5,695,525 | A | 12/1997 | Mulhauser et al. |
| 5,702,421 | A | 12/1997 | Schneidt |
| 5,709,707 | A | 1/1998 | Lock et al. |
| 5,716,397 | A | 2/1998 | Myers |
| 5,725,552 | A | 3/1998 | Kotula et al. |
| 5,733,294 | A | 3/1998 | Forber et al. |
| 5,741,297 | A | 4/1998 | Simon |
| 5,766,246 | A | 6/1998 | Mulhauser et al. |
| 5,846,261 | A | 12/1998 | Kotula et al. |
| 5,853,422 | A | 12/1998 | Huebsch et al. |
| 5,861,003 | A | 1/1999 | Latson et al. |
| 5,879,366 | A | 3/1999 | Shaw et al. |
| 5,904,703 | A | 5/1999 | Gilson |
| 5,919,200 | A | 7/1999 | Stambaugh et al. |
| 5,931,835 | A | 8/1999 | Mackey |
| 5,944,738 | A | 8/1999 | Amplatz et al. |
| 5,954,767 | A | 9/1999 | Pajotin et al. |
| 5,972,030 | A | 10/1999 | Garrison et al. |
| 6,007,557 | A | 12/1999 | Ambrisco et al. |
| 6,024,096 | A | 2/2000 | Buckberg |
| 6,024,756 | A | 2/2000 | Huebsch et al. |
| 6,077,281 | A | 6/2000 | Das |
| 6,077,291 | A | 6/2000 | Das |
| 6,080,182 | A | 6/2000 | Shaw et al. |
| 6,093,199 | A | 7/2000 | Brown et al. |
| 6,117,159 | A | 9/2000 | Huebsch et al. |
| 6,120,539 | A | 9/2000 | Eldridge et al. |
| 6,123,715 | A | 9/2000 | Amplatz |
| 6,126,673 | A | 10/2000 | Kim et al. |
| 6,127,597 | A | 10/2000 | Beyar et al. |
| 6,143,024 | A | 11/2000 | Campbell et al. |
| 6,152,144 | A | 11/2000 | Lesh et al. |
| 6,152,947 | A | 11/2000 | Ambrisco et al. |
| 6,159,240 | A | 12/2000 | Sparer et al. |
| 6,168,616 | B1 | 1/2001 | Brown, III |
| 6,171,329 | B1 | 1/2001 | Shaw et al. |
| 6,174,322 | B1 | 1/2001 | Schneidt |
| 6,190,218 | B1 | 2/2001 | Hall et al. |
| 6,200,336 | B1 | 3/2001 | Pavcnik et al. |
| 6,206,907 | B1 | 3/2001 | Marino et al. |
| 6,214,020 | B1 | 4/2001 | Mulhauser et al. |
| 6,214,029 | B1 | 4/2001 | Thill et al. |
| 6,221,092 | B1 | 4/2001 | Koike et al. |
| 6,231,561 | B1 | 5/2001 | Frazier et al. |
| 6,238,416 | B1 | 5/2001 | Sideris |
| 6,245,012 | B1 | 6/2001 | Kleshinski |
| 6,258,122 | B1 | 7/2001 | Tweden et al. |
| 6,258,124 | B1 | 7/2001 | Darois et al. |
| 6,267,776 | B1 * | 7/2001 | O'Connell .................... 606/200 |
| 6,267,777 | B1 | 7/2001 | Bosma et al. |
| 6,270,515 | B1 | 8/2001 | Linden et al. |
| 6,270,530 | B1 | 8/2001 | Eldridge et al. |
| 6,273,895 | B1 | 8/2001 | Pinchuk et al. |
| 6,273,901 | B1 | 8/2001 | Whitcher et al. |
| 6,290,674 | B1 | 9/2001 | Roue et al. |
| 6,312,446 | B1 | 11/2001 | Huebsch et al. |
| 6,312,447 | B1 | 11/2001 | Grimes |
| 6,319,268 | B1 | 11/2001 | Ambrisco et al. |
| 6,325,815 | B1 | 12/2001 | Kusleika et al. |
| 6,328,727 | B1 | 12/2001 | Frazier et al. |
| 6,332,892 | B1 | 12/2001 | Desmond, III et al. |
| 6,334,864 | B1 | 1/2002 | Amplatz et al. |
| 6,344,048 | B1 | 2/2002 | Chin et al. |
| 6,348,063 | B1 | 2/2002 | Yassour et al. |
| 6,355,052 | B1 | 3/2002 | Neuss et al. |
| 6,368,338 | B1 * | 4/2002 | Konya et al. .................... 606/200 |
| 6,368,339 | B1 | 4/2002 | Amplatz |
| 6,368,541 | B1 | 4/2002 | Pajotin et al. |
| 6,402,771 | B1 | 6/2002 | Palmer et al. |
| 6,416,549 | B1 | 7/2002 | Chinn et al. |
| 6,419,669 | B1 | 7/2002 | Frazier et al. |
| 6,419,695 | B1 | 7/2002 | Gabbay |
| 6,436,088 | B2 | 8/2002 | Frazier et al. |
| 6,440,152 | B1 | 8/2002 | Gainor et al. |
| 6,443,972 | B1 | 9/2002 | Bosma et al. |
| 6,447,531 | B1 | 9/2002 | Amplatz |
| 6,450,171 | B1 | 9/2002 | Buckberg et al. |
| 6,458,100 | B2 | 10/2002 | Roue et al. |
| 6,468,290 | B1 | 10/2002 | Weldon et al. |
| 6,468,303 | B1 | 10/2002 | Amplatz et al. |
| 6,482,222 | B1 | 11/2002 | Bruckheimer et al. |
| 6,482,224 | B1 | 11/2002 | Michler et al. |
| 6,506,204 | B2 | 1/2003 | Mazzocchi |
| 6,537,286 | B2 | 3/2003 | Acampora et al. |
| 6,537,300 | B2 | 3/2003 | Girton |
| 6,544,167 | B2 | 4/2003 | Buckberg et al. |
| 6,551,303 | B1 | 4/2003 | Van Tassel et al. |
| 6,551,344 | B2 | 4/2003 | Thill |
| 6,558,404 | B2 | 5/2003 | Tsukernik |
| 6,579,303 | B2 | 6/2003 | Amplatz |
| 6,596,013 | B2 | 7/2003 | Yang et al. |
| 6,599,308 | B2 | 7/2003 | Amplatz |
| 6,605,102 | B1 | 8/2003 | Mazzocchi et al. |
| 6,610,006 | B1 | 8/2003 | Amid et al. |
| 6,623,508 | B2 | 9/2003 | Shaw et al. |
| 6,641,557 | B1 | 11/2003 | Frazier et al. |
| 6,645,143 | B2 | 11/2003 | VanTassel et al. |
| 6,645,225 | B1 | 11/2003 | Atkinson |
| 6,652,555 | B1 | 11/2003 | VanTassel et al. |
| 6,652,556 | B1 | 11/2003 | VanTassel et al. |
| 6,656,206 | B2 | 12/2003 | Corcoran et al. |
| 6,673,089 | B1 | 1/2004 | Yassour et al. |
| 6,682,546 | B2 | 1/2004 | Amplatz |
| 6,689,150 | B1 | 2/2004 | VanTassel et al. |
| 6,702,835 | B2 | 3/2004 | Ginn |
| 6,712,804 | B2 | 3/2004 | Roue et al. |
| 6,712,835 | B2 | 3/2004 | Mazzocchi et al. |
| 6,712,836 | B1 | 3/2004 | Berg et al. |
| 6,723,133 | B1 | 4/2004 | Pajotin |
| 6,730,108 | B2 | 5/2004 | Van Tassel et al. |
| 6,736,823 | B2 | 5/2004 | Darois et al. |
| 6,736,854 | B2 | 5/2004 | Vadurro et al. |
| 6,740,112 | B2 | 5/2004 | Yodfat et al. |
| 6,740,122 | B2 | 5/2004 | Pajotin |
| 6,758,863 | B2 | 7/2004 | Estes et al. |
| 6,776,784 | B2 | 8/2004 | Ginn |
| 6,790,213 | B2 | 9/2004 | Cherok et al. |
| 6,797,083 | B2 | 9/2004 | Peterson |
| 6,837,247 | B2 | 1/2005 | Buckberg et al. |
| 6,911,037 | B2 | 6/2005 | Gainor et al. |
| 6,939,348 | B2 | 9/2005 | Malecki et al. |
| 6,949,113 | B2 | 9/2005 | Van Tassel et al. |
| 6,974,586 | B2 | 12/2005 | Greenhalgh et al. |
| 6,981,981 | B2 | 1/2006 | Reiley et al. |
| 6,994,092 | B2 | 2/2006 | van der Burg et al. |
| 7,001,406 | B2 | 2/2006 | Eskuri et al. |

(56) References Cited

U.S. PATENT DOCUMENTS

| | | |
|---|---|---|
| 7,052,498 B2 | 5/2006 | Levy et al. |
| 7,097,653 B2 | 8/2006 | Freudenthal et al. |
| 7,122,043 B2 | 10/2006 | Greenhalgh et al. |
| 7,128,073 B1 | 10/2006 | van der Burg et al. |
| 7,288,105 B2 | 10/2007 | Oman et al. |
| 7,452,371 B2 | 11/2008 | Pavcnik et al. |
| 7,581,328 B2 | 9/2009 | Greenhalgh et al. |
| 7,582,103 B2 | 9/2009 | Young et al. |
| 2001/0034537 A1 | 10/2001 | Shaw et al. |
| 2001/0037129 A1 | 11/2001 | Thill |
| 2001/0039434 A1 | 11/2001 | Frazier et al. |
| 2001/0039435 A1 | 11/2001 | Roue et al. |
| 2001/0041914 A1 | 11/2001 | Frazier et al. |
| 2001/0041915 A1 | 11/2001 | Roue et al. |
| 2002/0002401 A1 | 1/2002 | McGuckin et al. |
| 2002/0022860 A1 | 2/2002 | Borillo et al. |
| 2002/0026092 A1 | 2/2002 | Buckberg et al. |
| 2002/0035361 A1 | 3/2002 | Houser et al. |
| 2002/0062135 A1 | 5/2002 | Mazzocchi et al. |
| 2002/0068950 A1 | 6/2002 | Corcoran et al. |
| 2002/0072765 A1 | 6/2002 | Mazzocchi et al. |
| 2002/0077596 A1 | 6/2002 | McKenzie et al. |
| 2002/0087187 A1 | 7/2002 | Mazzocchi et al. |
| 2002/0095172 A1 | 7/2002 | Mazzocchi et al. |
| 2002/0095173 A1 | 7/2002 | Mazzocchi et al. |
| 2002/0123759 A1 | 9/2002 | Amplatz |
| 2002/0138095 A1 | 9/2002 | Mazzocchi et al. |
| 2002/0169474 A1 | 11/2002 | Kusleika et al. |
| 2002/0169475 A1 | 11/2002 | Gainor et al. |
| 2002/0183786 A1 | 12/2002 | Girton |
| 2002/0183787 A1 | 12/2002 | Wahr et al. |
| 2002/0198561 A1 | 12/2002 | Amplatz |
| 2002/0198563 A1 | 12/2002 | Gainor et al. |
| 2003/0018377 A1 | 1/2003 | Berg et al. |
| 2003/0028213 A1 | 2/2003 | Thill et al. |
| 2003/0036755 A1 | 2/2003 | Ginn |
| 2003/0045893 A1 | 3/2003 | Ginn |
| 2003/0045898 A1 | 3/2003 | Harrison et al. |
| 2003/0055455 A1 | 3/2003 | Yang et al. |
| 2003/0057156 A1 | 3/2003 | Peterson et al. |
| 2003/0097145 A1 | 5/2003 | Goldberg et al. |
| 2003/0120337 A1 | 6/2003 | Van Tassel et al. |
| 2003/0144694 A1 | 7/2003 | Chanduszko et al. |
| 2003/0153943 A1 | 8/2003 | Michael et al. |
| 2003/0167068 A1 | 9/2003 | Amplatz |
| 2003/0171772 A1 | 9/2003 | Amplatz |
| 2003/0171803 A1 | 9/2003 | Shimon |
| 2003/0181942 A1 | 9/2003 | Sutton et al. |
| 2003/0181945 A1 | 9/2003 | Opolski et al. |
| 2003/0187474 A1 | 10/2003 | Keegan et al. |
| 2003/0191495 A1 | 10/2003 | Ryan et al. |
| 2003/0191526 A1 | 10/2003 | Van Tassel et al. |
| 2003/0195530 A1 | 10/2003 | Thill |
| 2003/0195553 A1 | 10/2003 | Wallace et al. |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0208232 A1 | 11/2003 | Blaeser et al. |
| 2003/0212429 A1 | 11/2003 | Keegan et al. |
| 2003/0220667 A1 | 11/2003 | van der Burg et al. |
| 2003/0225421 A1 | 12/2003 | Peavey et al. |
| 2003/0225453 A1 | 12/2003 | Murch |
| 2004/0006368 A1 | 1/2004 | Mazzocchi et al. |
| 2004/0034366 A1 | 2/2004 | van der Burg et al. |
| 2004/0049210 A1 | 3/2004 | VanTassel et al. |
| 2004/0049226 A1 | 3/2004 | Keegan |
| 2004/0073242 A1 | 4/2004 | Chanduszko |
| 2004/0087968 A1 | 5/2004 | Core |
| 2004/0092973 A1 | 5/2004 | Chanduszko et al. |
| 2004/0093017 A1 | 5/2004 | Chanduszko |
| 2004/0098031 A1 | 5/2004 | van der Burg et al. |
| 2004/0098042 A1 | 5/2004 | Devellian et al. |
| 2004/0098047 A1 | 5/2004 | Frazier et al. |
| 2004/0098121 A1 | 5/2004 | Opolski |
| 2004/0102807 A1 | 5/2004 | Kusleika et al. |
| 2004/0122467 A1 | 6/2004 | VanTassel et al. |
| 2004/0127935 A1 | 7/2004 | VanTassel et al. |
| 2004/0133236 A1 | 7/2004 | Chanduszko |
| 2004/0153135 A1 | 8/2004 | Haase et al. |
| 2004/0167566 A1 | 8/2004 | Beulke et al. |
| 2004/0167613 A1 | 8/2004 | Yodfat et al. |
| 2004/0167625 A1 | 8/2004 | Beyar et al. |
| 2004/0176788 A1 | 9/2004 | Opolski |
| 2004/0176797 A1 | 9/2004 | Opolski |
| 2004/0176799 A1 | 9/2004 | Chanduszko et al. |
| 2004/0181253 A1 | 9/2004 | Sepetka et al. |
| 2004/0186486 A1 | 9/2004 | Roue et al. |
| 2004/0193147 A1 | 9/2004 | Malecki et al. |
| 2004/0215219 A1 | 10/2004 | Eldridge et al. |
| 2004/0220595 A1 | 11/2004 | Frazier et al. |
| 2004/0220596 A1 | 11/2004 | Frazier et al. |
| 2004/0230185 A1 | 11/2004 | Malecki et al. |
| 2004/0267191 A1 | 12/2004 | Gifford, III et al. |
| 2004/0267306 A1 | 12/2004 | Blaeser et al. |
| 2005/0021016 A1 | 1/2005 | Malecki et al. |
| 2005/0021076 A1 | 1/2005 | Mazzocchi et al. |
| 2005/0034735 A1 | 2/2005 | Deem et al. |
| 2005/0043759 A1 | 2/2005 | Chanduszko |
| 2005/0049573 A1 | 3/2005 | Van Tassel et al. |
| 2005/0080406 A1 | 4/2005 | Malecki et al. |
| 2005/0085843 A1 | 4/2005 | Opolski et al. |
| 2005/0085848 A1 | 4/2005 | Johnson et al. |
| 2005/0090857 A1 | 4/2005 | Kusleika et al. |
| 2005/0090858 A1 | 4/2005 | Pavlovic |
| 2005/0101984 A1 | 5/2005 | Chanduszko et al. |
| 2005/0101987 A1 | 5/2005 | Salahieh |
| 2005/0119689 A1 | 6/2005 | Mazzocchi et al. |
| 2005/0119690 A1 | 6/2005 | Mazzocchi et al. |
| 2005/0131401 A1 | 6/2005 | Malecki et al. |
| 2005/0131460 A1 | 6/2005 | Gifford, III et al. |
| 2005/0143827 A1 | 6/2005 | Globerman et al. |
| 2005/0149115 A1 | 7/2005 | Roue et al. |
| 2005/0177186 A1 | 8/2005 | Cully et al. |
| 2005/0177187 A1 | 8/2005 | Gray et al. |
| 2005/0192620 A1 | 9/2005 | Cully et al. |
| 2005/0192623 A1 | 9/2005 | Mazzocchi et al. |
| 2005/0192624 A1 | 9/2005 | Mazzocchi et al. |
| 2005/0192626 A1 | 9/2005 | Widomski et al. |
| 2005/0192654 A1 | 9/2005 | Chanduszko et al. |
| 2005/0203567 A1 | 9/2005 | Linder et al. |
| 2005/0203568 A1 | 9/2005 | van der Burg et al. |
| 2005/0203570 A1 | 9/2005 | Mazzocchi et al. |
| 2005/0203571 A1 | 9/2005 | Mazzocchi et al. |
| 2005/0203572 A1 | 9/2005 | Mazzocchi et al. |
| 2005/0203573 A1 | 9/2005 | Mazzocchi et al. |
| 2005/0203574 A1 | 9/2005 | Mazzocchi et al. |
| 2005/0209636 A1 | 9/2005 | Widomski et al. |
| 2005/0216051 A1 | 9/2005 | Mazzocchi et al. |
| 2005/0216052 A1 | 9/2005 | Mazzocchi et al. |
| 2005/0216054 A1 | 9/2005 | Widomski et al. |
| 2005/0251154 A1 | 11/2005 | Chanduszko et al. |
| 2005/0267523 A1 | 12/2005 | Devellian et al. |
| 2005/0267524 A1 | 12/2005 | Chanduszko |
| 2005/0267525 A1 | 12/2005 | Chanduszko |
| 2005/0273119 A1 | 12/2005 | Widomski et al. |
| 2005/0273124 A1 | 12/2005 | Chanduszko |
| 2005/0273135 A1 | 12/2005 | Chanduszko et al. |
| 2005/0288706 A1 | 12/2005 | Widomski et al. |
| 2005/0288786 A1 | 12/2005 | Chanduszko |
| 2006/0009799 A1 | 1/2006 | Kleshinski et al. |
| 2006/0015138 A1 | 1/2006 | Gertner |
| 2006/0027241 A1 | 2/2006 | Malecki et al. |
| 2006/0036284 A1 | 2/2006 | Blaeser et al. |
| 2006/0052821 A1 | 3/2006 | Abbott et al. |
| 2006/0058833 A1 | 3/2006 | VanCamp et al. |
| 2006/0064039 A1 | 3/2006 | Griego et al. |
| 2006/0089715 A1 | 4/2006 | Truckai et al. |
| 2006/0100706 A1 | 5/2006 | Shadduck et al. |
| 2006/0178694 A1 | 8/2006 | Greenhalgh et al. |
| 2006/0264980 A1 | 11/2006 | Khairkhahan et al. |
| 2007/0044811 A1* | 3/2007 | Deem et al. .......... 128/898 |
| 2007/0083227 A1 | 4/2007 | van der Burg et al. |
| 2007/0270905 A1 | 11/2007 | Osborne |
| 2008/0039743 A1 | 2/2008 | Fox et al. |

(56) References Cited

U.S. PATENT DOCUMENTS

| | | |
|---|---|---|
| 2008/0039804 A1 | 2/2008 | Edmiston et al. |
| 2008/0039922 A1 | 2/2008 | Miles et al. |
| 2008/0039929 A1 | 2/2008 | Davis et al. |
| 2008/0039952 A1 | 2/2008 | Linder et al. |
| 2008/0039953 A1 | 2/2008 | Davis et al. |
| 2008/0119886 A1 | 5/2008 | Greenhalgh |
| 2008/0119891 A1 | 5/2008 | Miles et al. |
| 2008/0161825 A1 | 7/2008 | Greenhalgh et al. |
| 2009/0275976 A1 | 11/2009 | Kleshinski et al. |
| 2010/0152767 A1 | 6/2010 | Greenhalgh et al. |

FOREIGN PATENT DOCUMENTS

| | | |
|---|---|---|
| EP | 0852132 | 7/1998 |
| EP | 1695673 | 8/2006 |
| JP | 11-309217 | 11/1999 |
| JP | 11-318910 | 11/1999 |
| JP | 11512641 | 11/1999 |
| JP | 2000-126304 | 5/2000 |
| JP | 2000-279533 | 10/2000 |
| JP | 2002-355248 | 12/2002 |
| JP | 2003529384 A | 10/2003 |
| JP | 2004-097807 A | 4/2004 |
| JP | 2004267796 A | 9/2004 |
| JP | 2006-189971 | 7/2006 |
| JP | 2007535986 | 12/2007 |
| JP | 2008514291 | 5/2008 |
| JP | 2009502229 | 1/2009 |
| WO | WO 00/44321 | 8/2000 |
| WO | WO 00/66031 | 11/2000 |
| WO | WO 00/69365 | 11/2000 |
| WO | WO 01/26726 | 4/2001 |
| WO | WO 01/54598 | 8/2001 |
| WO | WO 01/78625 | 10/2001 |
| WO | WO 03/082363 | 10/2003 |
| WO | WO 03/101312 | 12/2003 |
| WO | WO 2004/071343 A2 | 8/2004 |
| WO | WO 2004/103209 | 12/2004 |
| WO | WO 2004/110300 | 12/2004 |
| WO | WO 2005/034764 | 4/2005 |
| WO | WO 2006/126979 | 11/2006 |

OTHER PUBLICATIONS

Rigby, M. L., The era of transcatheter closure of atrial septal defects, *Heart*, 1999, 81:227-228.

Collins, Lois M., "Utah company's new stent may help repair heart defects," *Deseret News*, online article, Oct. 3, 2007, <http://deseretnews.com/article/content/mobile/1,5620,695215269,00.html?printView=true>.

Franklin et al., "Uptake of Tetracycline by Aortic Aneurysm Wall and Its Effect on Inflammation and Proteolysis," *Brit. J. Surger*, 86(6):771-775.

Pyo et al., "Targeted Gene Disruption of Matrix Metalloproteinase-9 (Gelatinase B) Suppresses Development of Experimental Abdominal Aortic Aneurysms," *J. Clinical Investigation*, 105(11):1641-1649.

Rao, P. S., "Summary and Comparison of Atrial Septal Defect Closure Devices," *Current Interventional Cardiology Reports*, 2:367-376, 2000.

Rigby, M. L., "The era of transcatheter closure of atrial septal defects," *Heart*, 81:227-228, 2000.

Tambiah et al., "Provocation of Experimental Aortic Inflammation Mediators and Chlamydia Pneumoniae," *Brit., J. Surgery*, 88(7):935-940.

Walton et al., "Inhibition of Prostoglandin E2 Synthesis in Abdominal Aortic Aneurysms," *Circulation*, 48-54, Jul. 6, 1999.

Xu et al., "Sp1 Increases Expression of Cyclooxygenase-2 in Hypoxic Vascular Endothelium," *J. Biological Chemistr*, 275(32):24583-24589.

Sievert et al.,"Percutaneous Closure of 176 Inter-Atrial Defects in Adults with Different Occlusion Devices- 6 Years Experience" (abstract). J. Am. Coll. Cardiol, 1999, 33: 519A-520A.

Bartel, T. et al., "Intracardiac Echocardiography is Superior to Conventional Monitoring for Guiding Device Closure of Interatrial Communications," Circulation, 107-795, 2003.

SAAB; Application of high-pressured balloons in the medical device industry; Advanced Polymers, Inc., 1999 (http://advpoly.com/Documents/MedicalBalloonPaper.pdf).

\* cited by examiner

Fetal Circulation

EMBOLIC FILTERING METHOD AND APPARATUS

CROSS-REFERENCE TO RELATED APPLICATIONS

This application is a continuation-in-part (CIP) of U.S. patent application Ser. No. 10/847,909, filed May 19, 2004, now U.S. Pat. No. 7,122,043, which is based on and claims priority to U.S. Provisional Patent Application No. 60/471,555, May 19, 2003, the entire disclosures of which are hereby incorporated by reference.

BACKGROUND OF THE INVENTION

1. Field of the Invention

The present invention relates generally to a device and method for preventing the undesired passage of emboli from a venous blood pool to an arterial blood pool. The invention relates especially to a device and method for treating certain cardiac defects, especially patent foramen ovales and other septal defects through the use of an embolic filtering device capable of instantaneously deterring the passage of emboli from the moment of implantation.

2. Description of Related Art

The fetal circulation is vastly different than the normal adult circulation. The blood circulating in a fetus is oxygenated by the placenta, not the developing lungs. Therefore, the fetal circulation directs only a small percentage of the circulating blood to the fetal lungs. Most of the circulating blood is shunted away from the lungs to the peripheral tissues through specialized vessels and foramens that are open ("patent" during fetal life. In most people these specialized structures quickly close after birth. Unfortunately, they sometimes fail to close and create hemodynamic problems that can be fatal if left untreated.

A diagram showing the blood circulation of a human fetus is illustrated in FIG. 1. The umbilical arteries branch off of the iliac arteries and deliver unoxygenated blood to the placenta. The fetal blood travels through the capillary bed in the placenta and transfers carbon dioxide to the maternal blood and takes oxygen and other nutrients from the maternal blood. The umbilical vein returns oxygenated blood to the fetus. Most of the oxygenated blood from the umbilical vein bypasses the developing liver and travels through a specialized vessel called the ductus venosus to the inferior vena cava and then into the right atrium. A good portion of the oxygenated blood from the inferior vena cava is directed across the right atrium and into the left atrium through a specialized curtain like opening in the heart called the foramen ovale. The blood from the left atrium then enters the left ventricle and then into the aorta where it travels to the head and other body tissues delivering the needed oxygen and nutrients.

The small amount of blood entering the right atrium that does not pass through the foramen ovale, most of which comes from the superior vena cava, flows into the right ventricle and then gets pumped into the pulmonary trunk and pulmonary arteries. Some of this blood is pumped into the developing lungs. However, the fetal lungs are collapsed which causes a high resistance to blood flow. Another specialized vessel, called the ductus arteriosus, is a vessel that connects the high pressure pulmonary artery to the lower pressure aorta. Therefore, most of the blood in the pulmonary artery flows into the lower pressure aorta through this specialized vessel.

Upon birth, the circulatory system goes through profound changes. The flow through the umbilical arteries and umbilical vein stops and consequently the flow through the musculature around the ductus venosus constricts and the blood flow through the ductus venosus stops. The lungs fill with air and the resistance to blood flow into the lungs drastically decreases. The corresponding pressure in the right atrium, right ventricle, and pulmonary arteries also decrease. The decrease in pressure in the right atrium causes the curtain like opening of the foramen ovale to close, driving more blood into the right ventricle and then to the lungs for oxygenation. Over time, the foramen ovale is replaced with a membrane called the fossa ovalis. Similarly, the decrease in pressure in the pulmonary arteries reduced the pulmonary arterial pressure to the same as or slightly less than the pressure in the aorta, which stops or reverses the flow through the ductus arteriosus. Once the muscular tissue of the ductus arteriosus is perfused with well oxygenated blood, the muscle begins to constrict and close the ductus arteriosus. The ductus arteriosus normally closes within about one week of life.

Usually over time, the unique openings of the fetal circulation become obliterated and a solid mass of tissue forms where these opening once were. However, in some people the opening remain. A patent ductus venosus after birth is very rare and almost always fatal. A patent ductus arteriosus occurs in about 1 out of every 5000 births. The patent ductus arteriosus once diagnosed is either medically treated or surgically ligated to close the ductus. In about one of four people, the foramen ovale does not seal shut, instead it remains patent. Such defects usually measure 10 mm or more in diameter and occupy one third or more of the length of the atrial septum in echocardiographic four chamber sections. Since the pressure in the left atrium is about two to four mm Hg greater than the pressure in the right atrium, the curtain like opening usually remains shut. However, if the pressure in the right atrium increases, such as upon heavy lifting or while performing a Valsalva type maneuver, the curtain like fold of tissue opens and the blood flows from the right atrium to the left atrium.

Studies have shown that adults with strokes of unknown origin, i.e., cryptogenic strokes, have about twice the normal rate of patent foramen ovales than the normal population. Although there is a correlation between strokes and patent foramen ovales, it is currently unknown why this correlation exists. It is theorized that blood clots and plaque that have formed in the peripheral venous circulation (in the legs for example) break off and travel to the heart. Normally, the clots and plaque get delivered to the lungs where it is trapped and usually cause no harm to the patient. Patients with a patent foramen ovale, however, have a potential opening that the clots or plaque can pass through the venous circulation and into the arterial circulation and then into the brain or other tissues to cause a thromboembolic event like a stroke. The clots may pass to the arterial side when there is an increase in the pressure in the right atrium. Then the clots travel through the left side of the heart, to the aorta, and then to the brain via the carotid arteries where they cause a stroke and the associated neurological deficits.

A number of atrial septal defects (ASD) closure devices have been developed and investigated in an attempt to develop a nonsurgical, transvenous method of occlusion of ASD. These include the Sideris Buttoned device, the Angel Wing Das device, the atrial septum defect occlusion system (ASDOS) device, the Amplatz Septal Occluder, the CardioSEAL/StarFlex devices, and the Gore/Helix devices. Unfortunately, each of these devices have distinct disadvantages and limitations ranging from the size of the device delivery sheath, ease of implantation, feasibility, safety and effectiveness. The Sideris buttoned device is made of a polyurethane foam occluder with a Teflon coated wire skeleton, which is positioned within the left atrium, and a polyurethane foam rhomboid shaped counterocculder with a Teflon coated wire skeleton, which is positioned in the right atrium. The major disadvantage with this device is the lack of a centering mechanism. For this reason, use of the devices at least two times the size of the stretched ASD is required. (Sievert H. Koppeler P. Rux S: Percutaneous closure of 176 interarterial defects in adults with different occlusion devices—6 years of experience [abstract], J. Am. Coll. Cardiol 1999, 33:519A.) Consequently, closure of defects may become difficult because the required size may be too large for the atrial septum to accommodate, or the device may impinge critical structures. There are also reports that the retrieval of the Sideris button device after incorrect deployment is difficult. (See, e.g., Rigby, Michael L., The Era of Transcatheter Closure of Atrial Septal Defects, Heart; 81:227-228 (1999)).

The "Angel Wings" device comprises two square frames made of superelastic Nitinol wire, each square frame having four legs that are interconnected by flexible islets at the corners. The wire frames are covered by polyester fibers. There is a conjoint suture ring of the right and atrial discs, which allow self centering on deployment. The device is delivered through an 11-13 F Mullins sheath. The major disadvantage of using this device is the attendant risk of aortic perforation cause by its sharp eyelet corners. In fact, the Angel Wings device was withdrawn from further clinical trials because of this problem. (Syamaxundar Rao, P., M.D., Summary and Comparison of Atrial Septal Defect Closure Devices, Current Interventional Cardiology Reports 2000, 2:367-376 (2000)). The device is also ill-suited for treating fenestrated defects.

The atrial septal defect occlusion system (ASDOS) prosthesis (Microvena Corp., White Bear Lake, Minn.) consists of two umbrellas made of Nitinol and a patch or porous polyurethane attached to the left and right atrial devices. The device is introduced transvenously over a long veno-arterial guidewire and through an 11 F venous transeptal sheath. While the device is retrievable in the event of malpositioning before release of the device, it requires a complex procedure to implant, and the components are known to have high incidences of thrombosis thrombosis. It is also reported that frame fractures have been detected in 20% of the patients treated with this device.

The Amplatzer device is the subject of U.S. Pat. No. 5,944,738 to Amplatzer, et al. This device is a saucer-shaped device formed from a mesh of fine Nitinol wires with a central connecting cylinder having a diameter similar to that of the stretched diameter of the defect. Thrombosis following implantation of the device is induced by three polyester patches. The device is delivered through a 6-10 F Mullins sheath. The primary disadvantage with this device is that it is ill-suited for closing fenestrated defects. Moreover, the device is a thick, bulky profile which dramatically increases the chances that the device will interfere with the heart's operation. Another disadvantage is its known capacity for incomplete endothelialisation with thrombus formation.

The CardioSEAL® device (NMT Medical, Inc.) is the subject of U.S. Pat. No. 6,206,907 to Marino, et al. This occlusion device is comprised of a center section to which stranded wire elastic shape memory fixation devices are attached. The fixation devices hold the occlusion devices in place once it is inserted into an aperture. Attached to the fixation devices are polyvinyl foam sheets which occlude the aperture. While the CardioSEAL is deemed to be relative easy to use, it is reported that, of all the devices, the CardioSEAL device has the highest incidence of arm fractures, which have raised serious issues concerning its safety. Moreover, the CardioSEAL device, like the Amplatzer device is relatively large, and requiring at least a 10 F or 11 F delivery systems, and an undue amount of hardware within the heart. These characteristics increase the chance that the device will interfere with the heart's operation, lend to residual shunting and/or embolization. The size of the CardioSEAL device also renders it less suitable for small children.

The STARflex® device (NMT Medical, Inc.) is an updated version of the CardioSEAL device, which includes a self-centering mechanism consisting of four flexible springs which pass between the two fabric disks. While this added feature may reduce the instances of residual shunting, the aforementioned defects and disadvantages of the CardioSEAL are still a concern.

In view of these drawbacks and related-risks, the method of choice to close a patent foramen ovale is still open heart surgery and ligation of the foramen ovale to close it. Surgery, however, is obviously associated with the usually risks of general anesthesia, open heart procedures, infections, etc. Thus, there is a need for a safe, cost-effective, and easily implantable device and method for preventing the passage of emboli from an arterial blood pool and a venous blood pool which is not subject to the defects and disadvantages of known devices.

SUMMARY OF THE INVENTION

The present invention is a directed to an embolic filtering apparatus for treating septal defects, including patent foramen ovales. In one preferred embodiment particularly suited for treating patent foramen ovales, the embolic filtering device comprises an embolic filter, composed of metal, fiber, and/or polymer, for preventing the passage of emboli through the septal defect, and a frame which allows the device to be secured within and or adjacent to the lumen of the septal defect.

The embolic filter is made by, for example, (1) swaging one end of a piece of tubular mesh at a first end with a first fastener (2) pulling the free end of the mesh over the first fastened end so that it overlaps the first portion; (3) swaging a second, center section of the tubular section to form a 3-dimensional ball-like structure having a first diameter portion with a second fastener; (4) extending the remaining free end of the tubular mesh back over the 3 dimensional ball-like structure of the first and second portions of the tubular mesh; and (4) swaging the free end of the tubular mesh with a third fastener to form an exterior 3-dimensional ball-like structure having a second diameter portion, within which the 3-dimensional ball-like structure of first diameter portion is disposed.

The mesh is removably secured to at least one or more bases of the frame, and positioned between the arms thereof. In a preferred embodiment, the bases of the frame and the fasteners which secure the tubular mesh are collars, having central lumens. The aforementioned third-fastener is insertable into the lumen of at least one of the bases of the frame in order to secure the mesh to the frame. The lumens of the fasteners and bases are aligned along a common axis in order that the embolic filtering device can be loaded onto a guide wire.

In an exemplary embodiment, the frame, preferably composed of metal, fabric and/or a polymer, includes at least one base and at least two arms which extend therefrom, between which the mesh is at least partially disposed. The arms are positioned opposite one another and, in their resting state, are spaced apart from one another. When, as in a preferred embodiment, the device is composed of a shape memory metal, such as nitinol, the device can is be collapsed into a catheter tube by compressing the arms of the frame toward one another, causing the length of the device to increase, and the width to decrease. As the device is released from the catheter tube, it reverts to its functional, relaxed state. The embolic filtering device may also be composed of non-shape memory metals, such as elgiloy, cobalt chromium, and stainless steel, for example. Each arm includes at least one anchor positioned on the arms of the frames. The anchors can either be arcuate or linear in formation, depending on the shape of the patent foramen ovale to be treated, and are of sufficient rigidity to secure the device within the lumen of a septal defect.

To allow for non-invasive visualization of the device within a subject at least a portion of the frame or mesh is composed of or coated with a radiopaque material, such as tantalum. The device may also be treated with thrombin, collagen, hyluron, or a host growth factor to encourage and facilitate growth of tissue onto the device so as to further secure the device within the septal defect. The device can also be coated with an anticoagulant to deter formation of blood clots on the surface of the device.

In an exemplary embodiment, the mesh is composed of at least 96 strands of 0.002" diameter wire braided such that the wires are situated at an angle of 35° relative to the longitudinal axis of the device. The interstices created by the braided wires are small enough such as to effectively filter emboli, thereby preventing emboli from passing through the patent foramen ovale, or other septal defect.

In another aspect of the invention, provided is a method of preventing the passage of emboli between a venous blood pool and an arterial blood pool by delivering the embolic filtering device to within, proximate to and/or adjacent to a passage between a venous blood pool and an arterial blood pool; and securing the device within, proximate to, and/or adjacent to said passage. The delivery of the device is preferably delivered by means of a catheter to within and/or adjacent to the passage between the venous blood pool and the aterial blood pool.

DETAILED DESCRIPTION OF THE INVENTION

Figure 1:
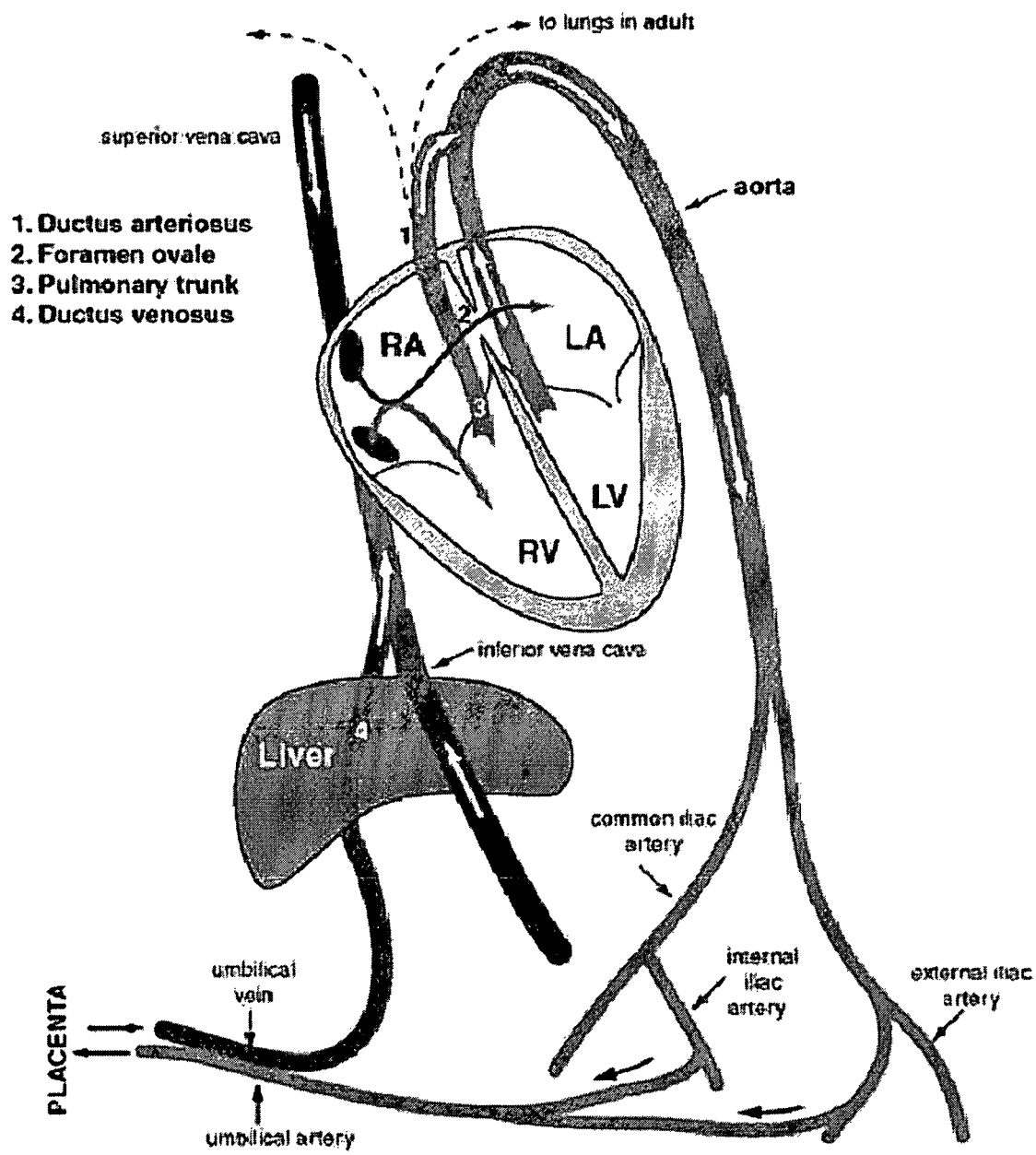
FIG. 1 is a schematic diagram of the fetal circulation.
Figure 2A:
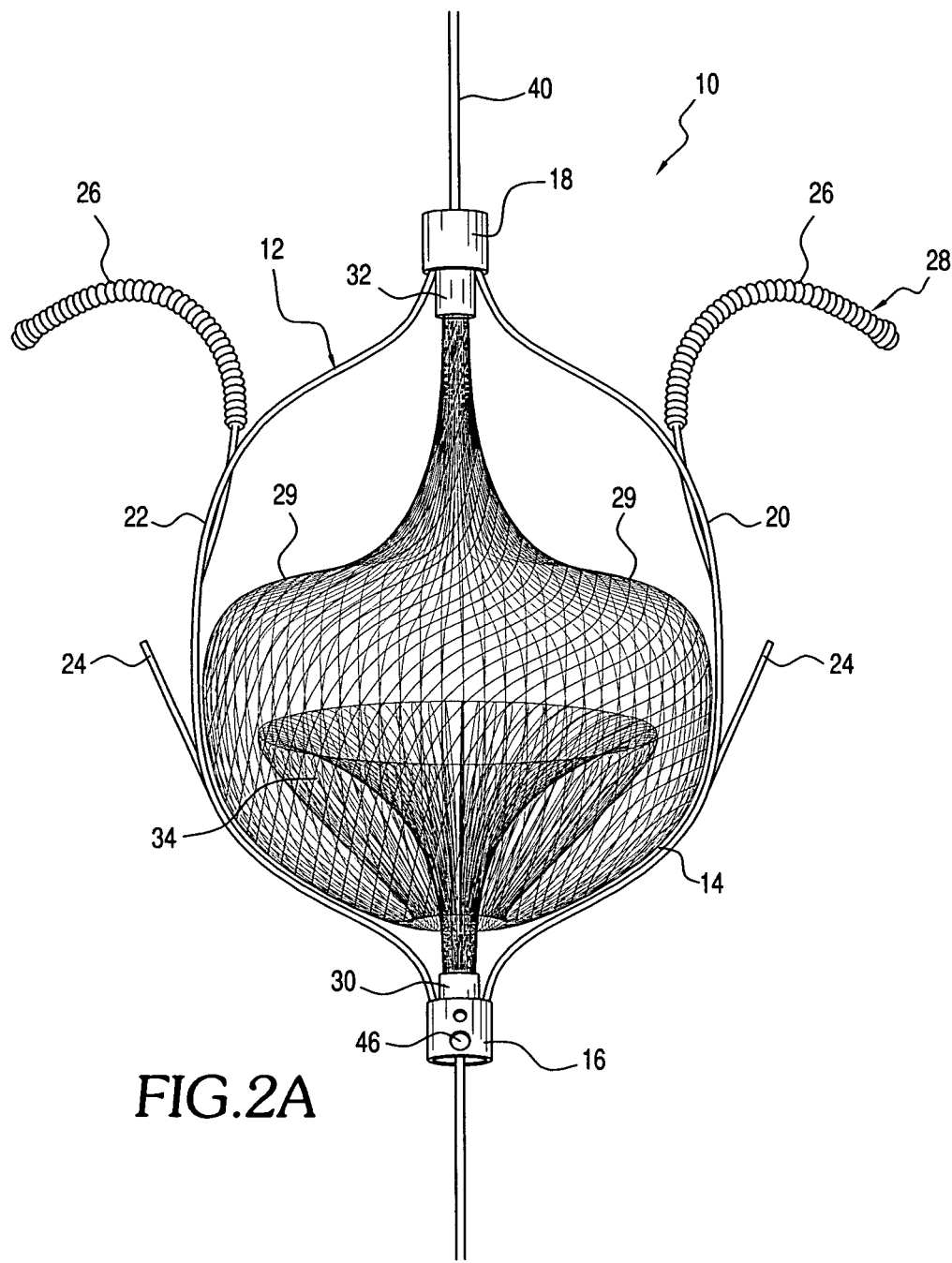
FIG. 2A illustrates a preferred embolic filtering device.
Figure 2B:
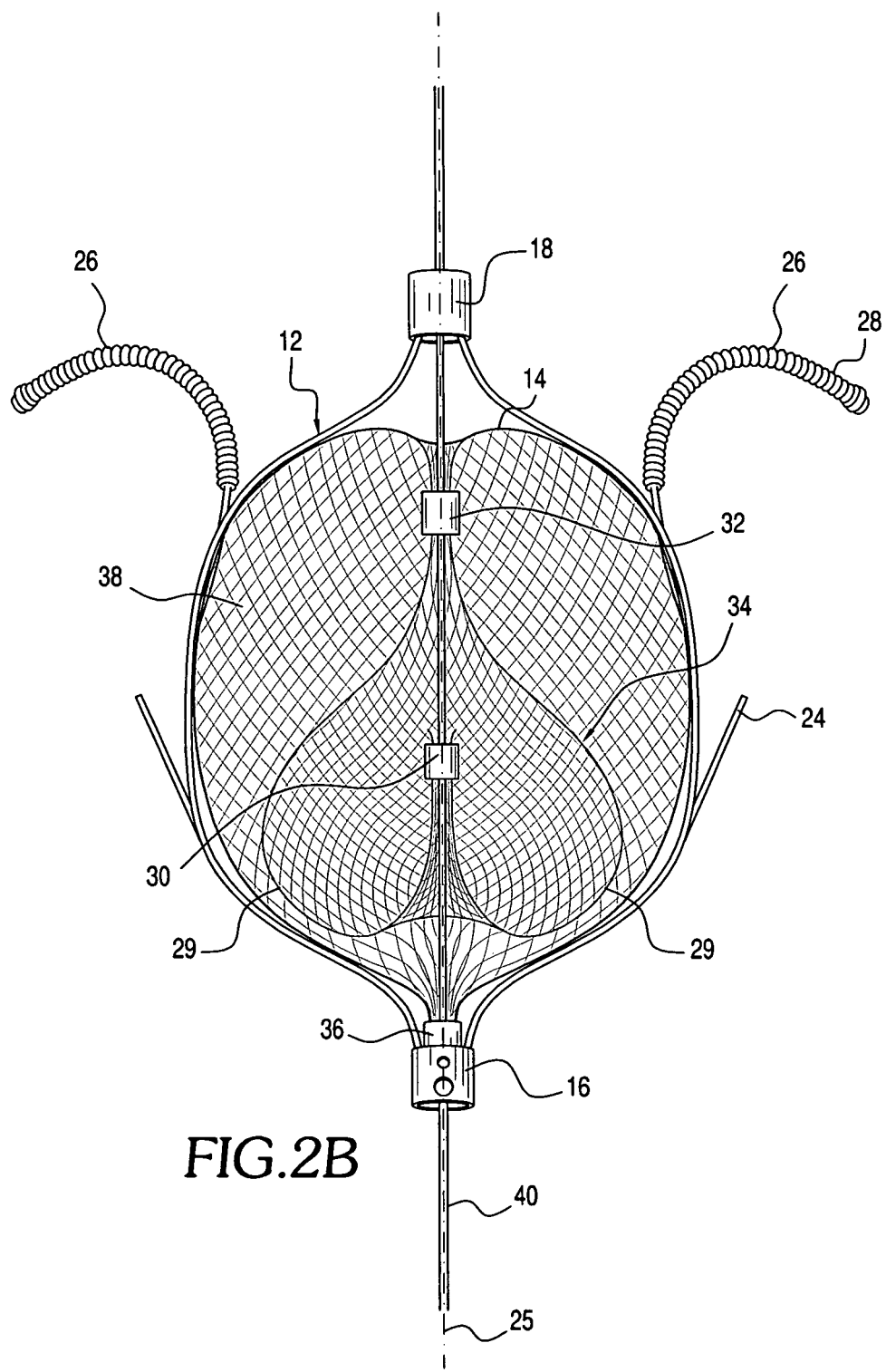
FIG. 2B illustrates another preferred embolic filtering device.

The present invention is directed generally to methods and apparatus for preventing the passage of emboli between a venous blood pool and an arterial blood pool using devices for creating a barrier to the conducting of emboli at a passage between a venous blood pool and an arterial blood pool. The device is particularly suitable for treating cardiac defects, such as patent foramen ovale or other atrium septal defects. In a preferred embodiment, exemplified at FIG. 2A, provided is an embolic filtering device 10 comprising a frame 12 and an embolic filter 14 comprising a mesh of stranded fabric, wire, or polymer. FIG. 2D illustrates one embodiment of frame 12 without embolic filter 14 attached. In this embodiment, frame 12 consists of a first base 16 and a second base 18. Each end of arms 20 and 22 are connected to first base 16 and second base 18, such that the lumens of first base 16 and second base 18 are in line with longitudinal axis 24 of frame 12. Arms 20 and 22 are preferably formed of a shape memory metal, e.g., nitinol, and formed such that, in the resting state, they are spaced apart from one another.

Referring to FIG. 2A, extending laterally from each of arms 20 and 22 proximate to first base 16 are right anchors 24. Right anchors 24 can be of any shape or formation suitable for delivering embolic filtering device 10 to the desired location and securing it in place. In a preferred embodiment, right anchors 24 are preferably linear or arcuate, and extend outward from frame 12 and away from first base 16, in the direction of second base 18, at an acute angle relative to longitudinal axis 25. The desired length of right anchors 24 and the position from which they extend from arms 20 and 22 will depend primarily on the size of the passage or defect to be treated. In any event, the right anchors 24 are of sufficient length to securely engage tissue within and/or adjacent to the septal defect. For example, when treating a patent foramen ovale, right anchors 26 preferably engage tissue within and/or adjacent to the right-atrial opening of the patent foramen ovale. Extending arcuately and/or laterally from the portion of arms 20 and 22 proximate second base 18 are left anchors 26. Left anchors 26 can be of any shape or formation suitable for delivering embolic filtering device 10 to the desired location and securing it in place; however, it has been found that arcuate or coiled anchors are most suitable for effectively securing the device within the area of interest. As with right anchors 24, left anchors 26 are of sufficient length to securely engage tissue within and/or adjacent to the septal defect to be treated. For example, when treating a patent foramen ovale, left anchors 26 preferably engage tissue within and/or adjacent to the left-atrial opening patent foramen ovale. In a preferred embodiment, right anchor 24 and left anchor 26 are covered with tantalum coil 28, or other radiopaque material, to allow for visualization of the position and location of embolic filtering device 10 after implantation in a subject. First base 16 and second base 18 and, for that matter, any portion of device 10 can likewise be compromised of radiopaque materials to provide even more visual points of reference in the imagery of embolic filtering device 10.

Figure 3:
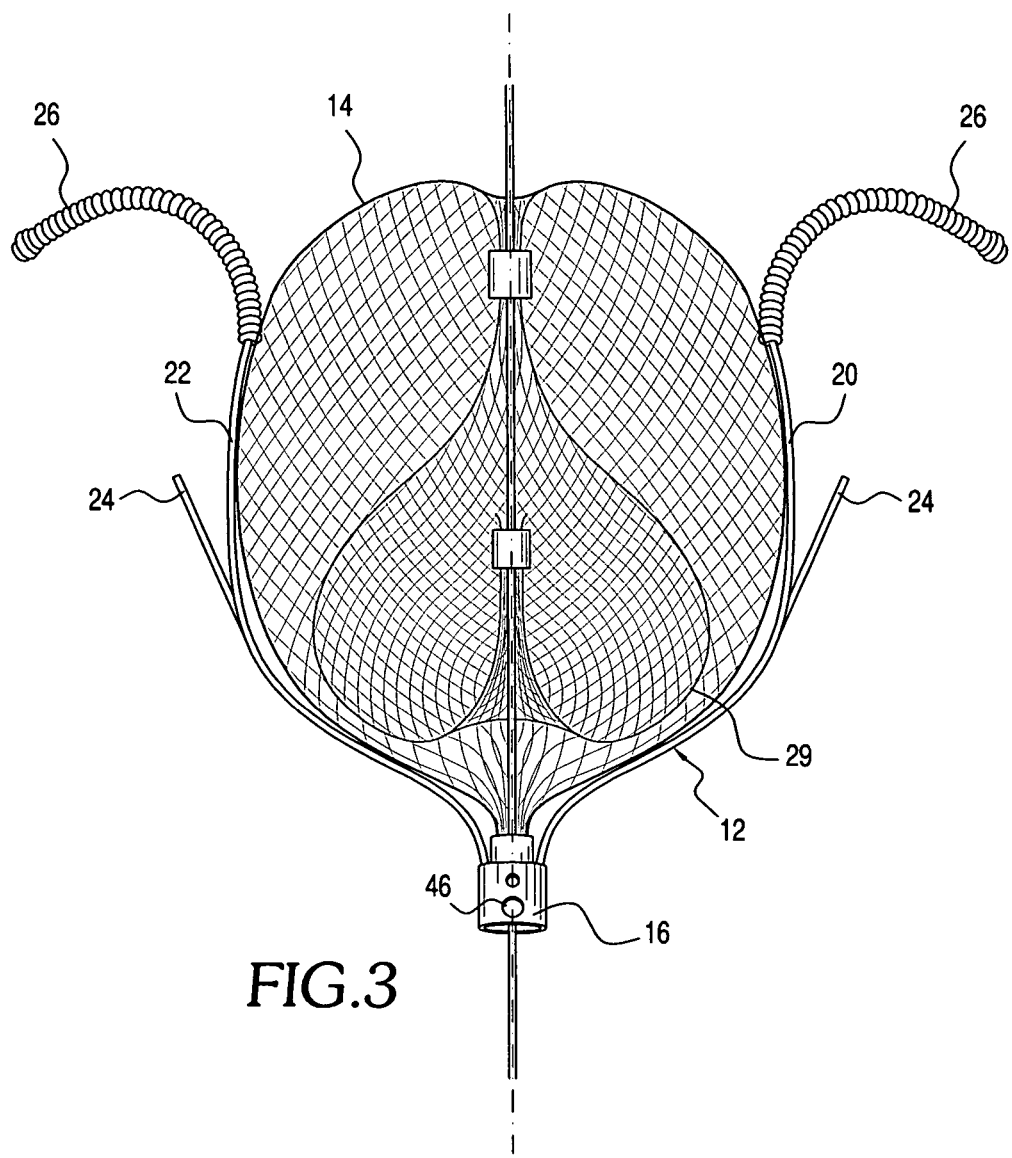
FIG. 3 illustrates another preferred embolic filtering device with a frame having one base.

In another embodiment illustrated in FIG. 3, provided is a frame 12 having first base 16, but without second base 18, and shortened arms 20 and 22. By eliminating second base 18, the amount of hardware implanted in the passage to be treated is minimized. Since, as discussed below, second base 18 resides closest to the left atrium of the heart when embolic filtering device 10 is used to treat a patent foramen ovale, eliminating second base 18 minimizes the amount of hardware adjacent to or within the left atrium, decreasing the chance the operation of the left atrium will be comprised, and reducing the surface area upon which blood clots can form.

Embolic filter 14 is removably coupled to frame 12, and is preferably comprised of plurality of braided wire strands having a predetermined relative orientation and interstitial space between the strands. Those skilled in the art will appreciate that the number and diameter of the wires used may be varied to achieve the desired density and stiffness of the fabric, and the known size of the emboli sought to be filtered. In a preferred embodiment, the wire mesh consists of at least 96 strands of 0.002" diameter wire, situated at an angle of approximate 35° relative to the longitudinal axis 25. Suitable wire strand materials ma be selected from a group consisting of a cobalt-based low thermal expansion alloy referred to in the field as "Elgiloy," nickel-based high temperature high-strength "superalloys" (including nitinol), nickel-based treatable alloys, a number of different grades of stainless steel, and polymers, including polyester, nylon, polytetrafluoroethylene (PTFE), polyurethane, polyaryletheretherketone (PEEK), and polyglycolic acid (PGA), polylactide (PLA), polyepsilon-caprolactone, polyethylacrylate (PEA). Platinum and alloys of platinum can also be co-braided, co-knitted or co-woven into mesh 14 to assist in determining where mesh is positioned within the patent foramen ovale. In a preferred embodiment, the wire strands are made from a shape memory alloy, NiTi (known as nitinol) which is an approximately stoichiometric alloy of nickel and titanium and may also include minor amounts of other metals to achieve desired properties. The frame 12 of device 10, and its components, including base 16, base 18, right arms 20 and left arms 22, are also preferably manufactured from so called shape memory alloys. Such alloys tend to have a temperature induced phase change which will cause the material to have a preferred configuration which can be fixed by heating the material above a certain transition temperature to induce a phase change in the material. When the alloy is cooled, the alloy will "remember" the shape it was in during the heat treatment and will tend to assume that configuration, unless constrained from doing so.

Handling requirements and variations of NiTi alloy compositions are known in the art. For example, U.S. Pat. No. 5,067,489 (Lind) and U.S. Pat. No. 4,991,602 (Amplatz et al.), the entire teachings of which are herein incorporated by reference, discuss the use of shape memory NiTi alloys in guide wires. Such NiTi alloys are preferred, at least in part, because they are commercially available and more is known about handling such alloys than other known shape memory alloys. NiTi alloys are also very elastic and are said to be "superelastic" or "pseudoelastic." This elasticity allows device 10 to return to a preset configuration after deployment from a catheter or other delivery device. The relaxed configuration is generally defined by the shape of the fabric when it is deformed to generally conform to the molding surface of the mold in which it was created. The wire stands are manufactured by standard braiding processes and equipment.

Figure 2C:
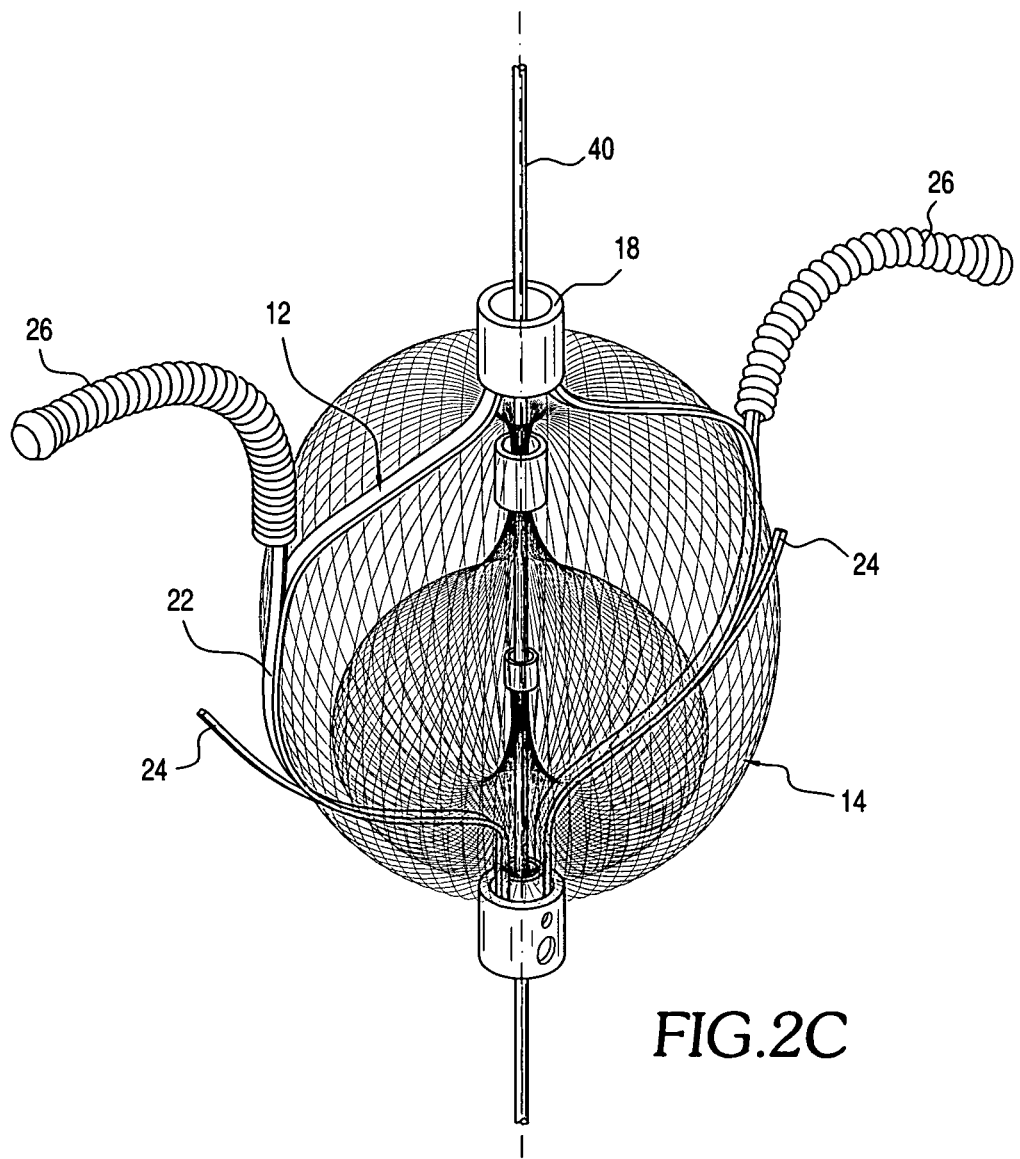
FIG. 2C illustrates a top view of the embolic filtering device illustrated in FIG. 2B.
Figure 2D:
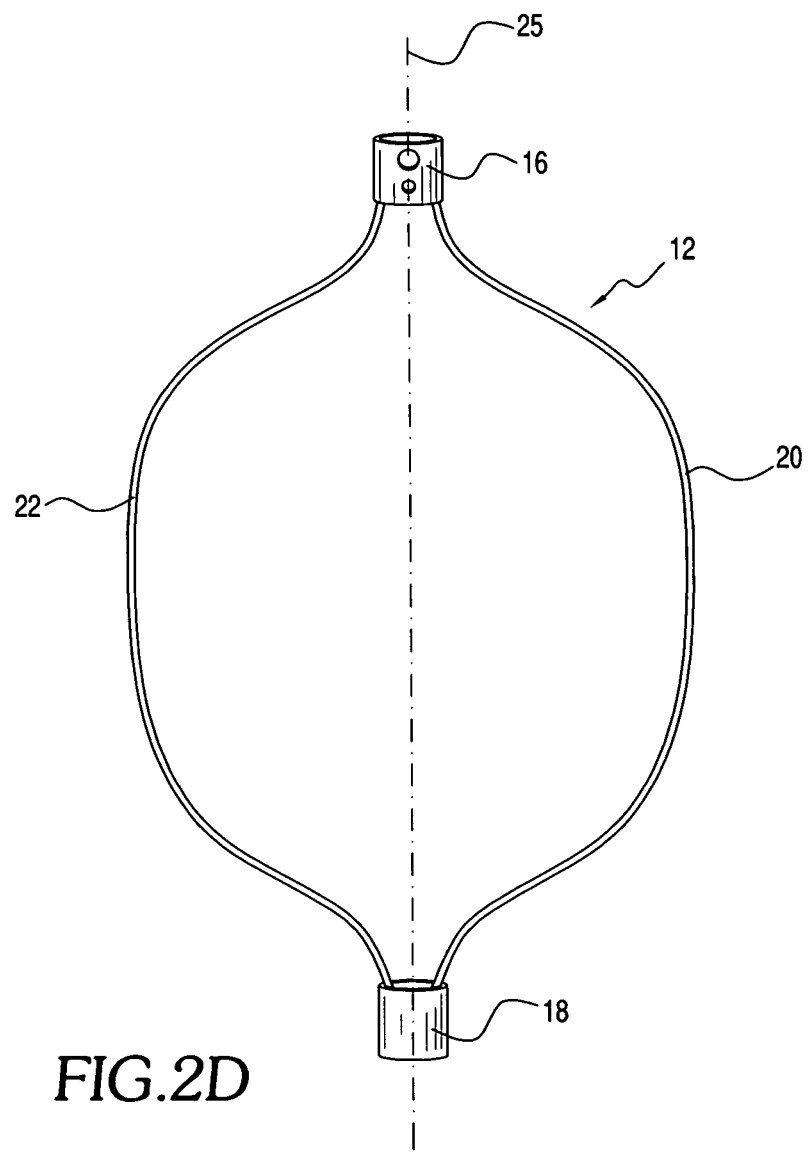
FIG. 2D illustrates a preferred frame of the embolic filtering having two bases.

Embolic filter 14 of the present invention is preferably in the shape of a three-dimensional ball or sphere, as exemplified in FIGS. 2A and 2C. Starting with a tubular piece of braided mesh or the like, the three-dimensional ball or sphere, as exemplified in FIG. 2A, is, for example, made by swaging a first end of the mesh with a first fastener 30, and pushing said first fastener 30 upwards into the lumen of the tubular mesh, to create interior lobes 29. A center portion of the mesh is then swaged with a second fastener 32, creating an interior embolic filter portion 34. The remaining mesh is then extended back over said first fastener 30 and interior embolic filter portion 34, and the second end of the braided tubular mesh is swaged with a third fastener 36. First fastener 30, second fastener 32, and interior embolic filter portion 34 are in effect situated within exterior embolic filter portion 38. Third fastener 30 is situated outside of said exterior embolic portion 38. In a preferred embodiment, fasteners 30, 32 and 36 are collars having a central lumen. The lumens of the collars are substantially aligned along a common longitudinal axis 24, and dimensioned to receive a guide wire 40. Embolic filter 14 is preferably secured to frame 12 by inserting third fastener 36 into the lumen of first base 16 of frame 12. To reduce the chance of third fastener 36 from disengaging from first base 16, third fastener 36 and first base 16 can be coupled together, either by a mechanical locking means such as that created by a press fit, as melted polymer interlock, or lint melt adhesive, or by plasma welding. Plasma welding, is the preferred coupling method, as it allows first base 16 to be shorter, since no portal is required on the base. When coupled to frame 12, embolic filter 14 resides at least partially between arms 20 and 22, such that the lumens of fasteners 30, 32, and 36 are substantially aligned with the lumens of first base 16 and second base 18 (if employing a frame with second base 18), along longitudinal axis 25. A plug composed of collagen, fabric, an adhesive, polymer or foam, for example, may be disposed within the aforementioned sphere to further deter the passage of embolic through the mesh.

In another preferred embodiment, illustrated in FIG. 2A, provided is an embolic filter 14 which, instead of having a spherical shape as exemplified in FIGS. 2B and 3, has a first end comprising at least one lobe-like formation and a second end which tapers inward therefrom. To make this embodiment, a piece of tubular mesh of suitable length, for example, is swaged at a first end by a first fastener 30. This first fastened end is then pushed into the lumen of the tubular mesh to form lobes 29. The second end of the mesh is then swaged by a second fastener 32. This embodiment is attached to frame 12 by securing first fastener in the lumen of base 16, and securing second fastener 32 in the lumen of base 18. As discussed above, fasteners 30 and 32 are collars having central lumens. The lumens of the collars are substantially aligned along a common longitudinal axis, and dimensioned to receive a guide wire 40.

Figure 5A:
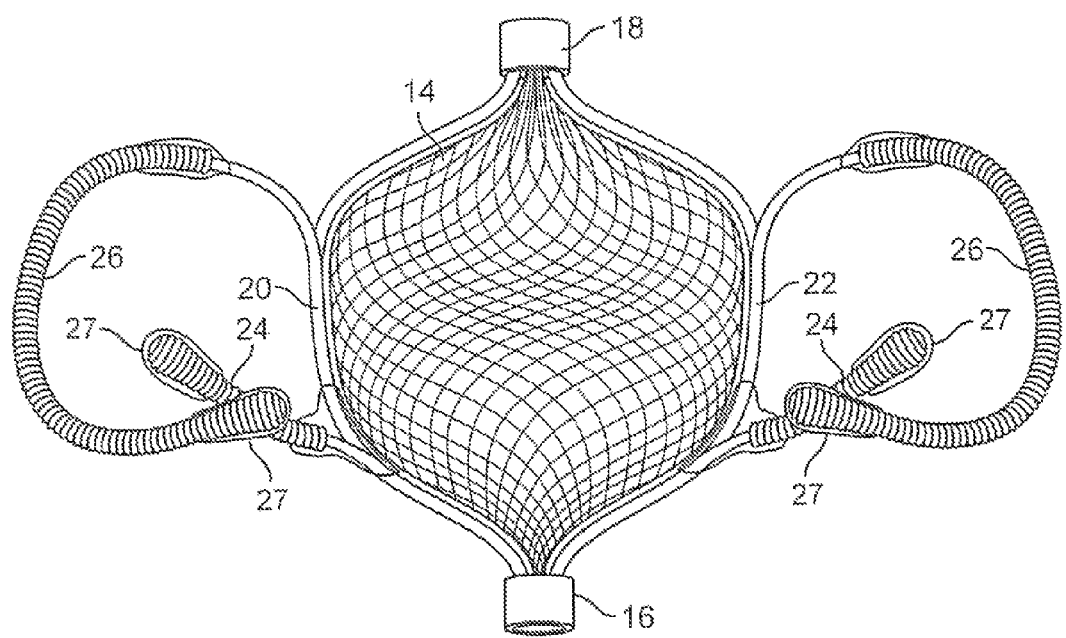
FIG. 5A illustrates another preferred embolic filtering device.
Figure 5B:
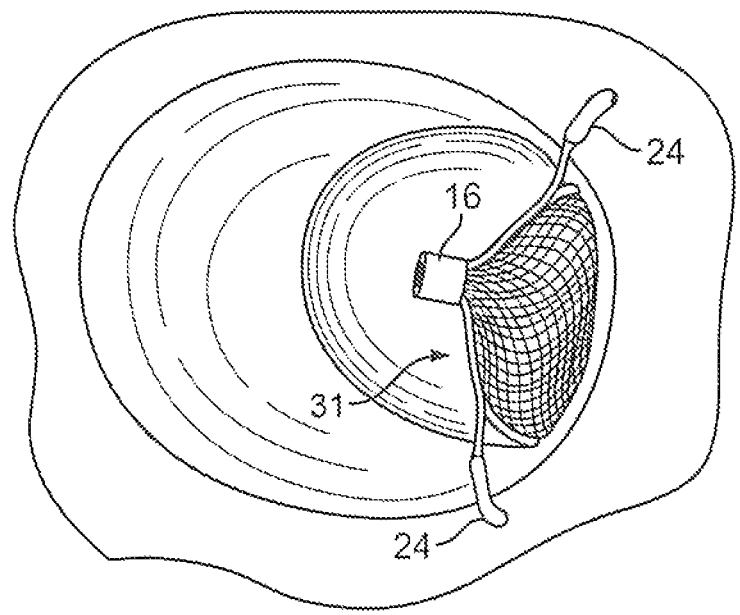
FIGS. 5B and 5C illustrate a preferred embolic filtering device within a patent foramen ovale.

In another preferred embodiment, illustrated in FIG. 5A, provided is an embolic filtering device 10, similar to those embodiments described above, but having right anchors 24 which are specifically designed to engage the perimeter of the tissue defining the right-atrial opening 23 of the patent foramen ovale, as illustrated in FIG. 5B. Contrary to right anchors 24 discussed in the aforementioned figures, the ends aright anchors 24 of this embodiment reside against or adjacent to the outside of the tissue wall defining the patent foramen ovale. Right anchors 24 are, therefore, preferably of slightly longer dimension and at least slightly arcuate in shape to facilitate this methodology. The ends of right anchors 24 in this embodiment, include protective caps 27 at their distal ends. Caps 27 can be composed of rubber, plastic, or any other suitable material for covering the ends of anchors 24 and 26, and may also comprise radiopaque materials, for example. In order to allow post-implant visualization of the location and positioning of anchors 24 after implant.

It will be recognized by those of ordinary skill that the manner in mesh 14 can be manufactured in a variety of ways without departing from the scope of the invention. For example, it will be recognized that mesh 14 does not necessarily need to be spherical, or have both an interior and exterior embolic portion, as discussed above. Mesh 14 can be of any shape and dimension suitable to deter the passage of embolic material between a venous blood pool and an arterial blood pool, and can include any number of layers, so long as the interstices between the strands forming mesh 14 are of sufficient area to filter emboli.

Figure 6A:
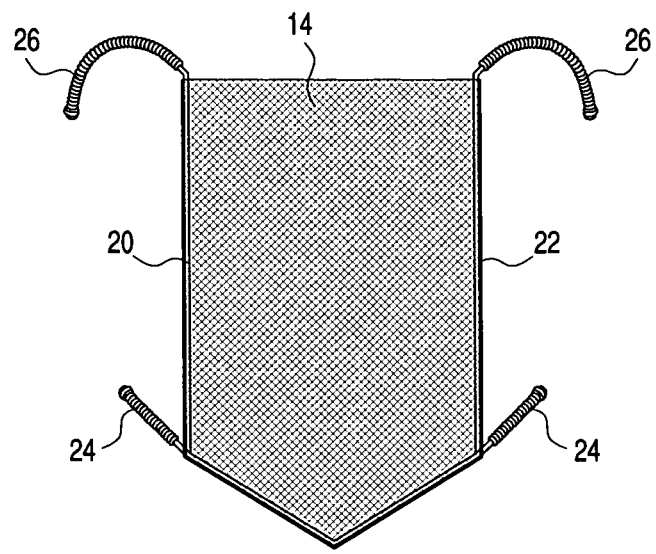
FIGS. 6A and 6B illustrate another preferred embolic filter device.
Figure 6B:
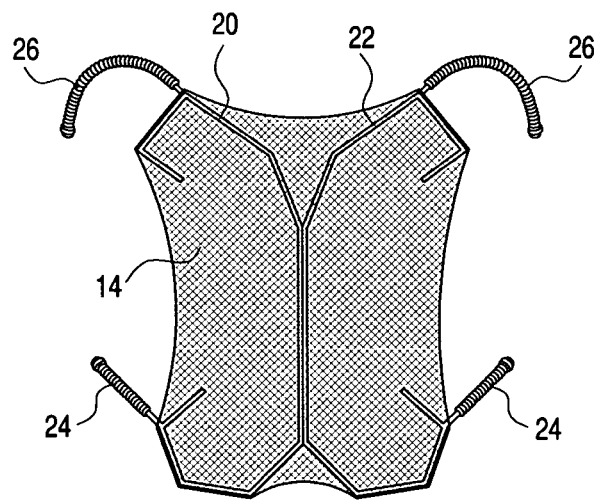
Figure 7A:
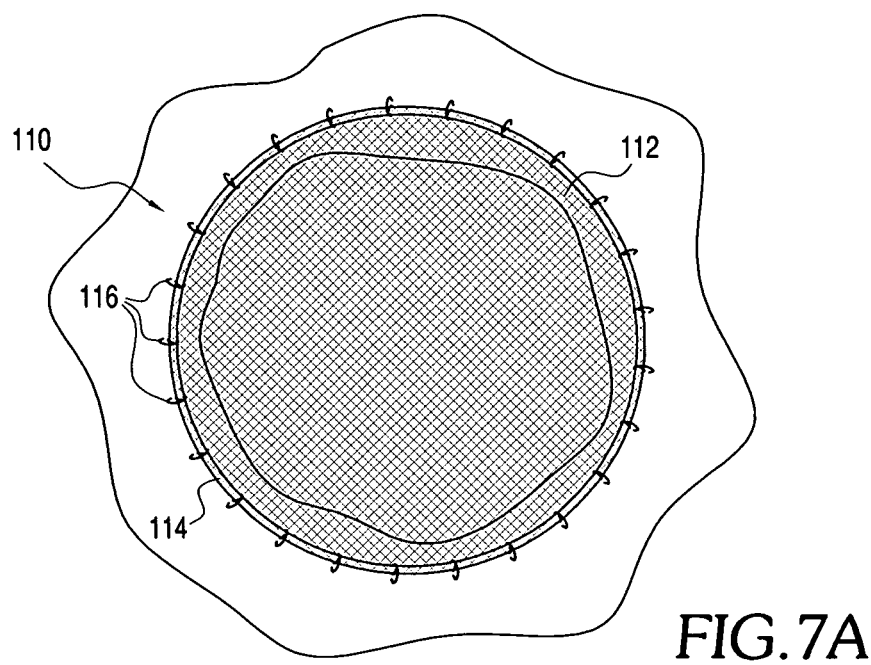
FIGS. 7A and 7B illustrated another preferred embolic filter device.
Figure 7B:
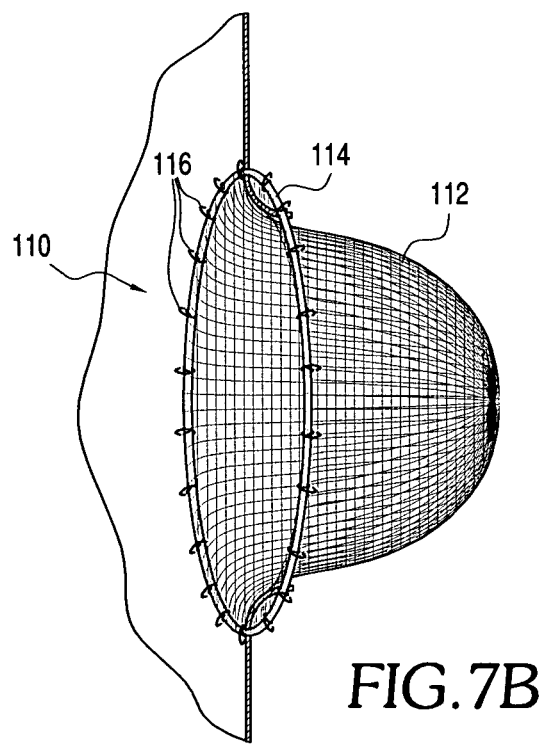

The design and dimensions of frame 12 can also be manufactured in a variety of ways without departing from the scope of the invention. FIGS. 6A and 6b illustrate yet a further embodiment of the invention, wherein arms 20 and 22 are effectively decoupled from one another, such that the tissue distension function of embolic filtering device 10 is provided separately by each individual legs of the device. This allows embolic filtering device 10 to be more compact, and to better fill gaps and meet the contours of the patent foramen ovale. Particularly with respect to the embodiments shown in FIGS. 6A and 6B, should be recognized that the size of mesh 14 need not be large, but can cover only arms 20 and 22 and still be effective in treating patent foramen ovales.

Device 10 provides distinct advantages and improvements over known patent foramen ovale-treatment devices. First, the elasticity and ball-like structure of mesh 14, enables device 10 to treat a patent foramen ovales, or other septal defects, of any shape and dimension with equal effectiveness. This is because mesh 14 is compressible along its entire length. Thus, it does not matter if the patent foramen ovale is fenestrated, as the elasticity of mesh 14 will allow it to conform to the substantially exact shape and dimension of the patent foramen ovale. Mesh 14 can also be annealed to have a 3-dimensional to help fill any gaps within the patent foramen ovale space. Thus, the post-implant leakage along the perimeter of known devices caused by their inability to accommodate irregular shaped defects is eliminated. Second, device 10 has substantially less surface compared to known devices, thereby reducing the risk of dangerous blood clot formation on the exterior of the device. Third, contrary to known devices which do not prevent passage of emboli through the defect until tissue growth onto the device occludes the defect, the interstices between the stands of braided mesh 14 of the present invention are small enough to effectively filter emboli as soon as device 10 is implanted. Thus, device 10 offers immediate protection against the passage of emboli at the moment of implant.

Figure 4:
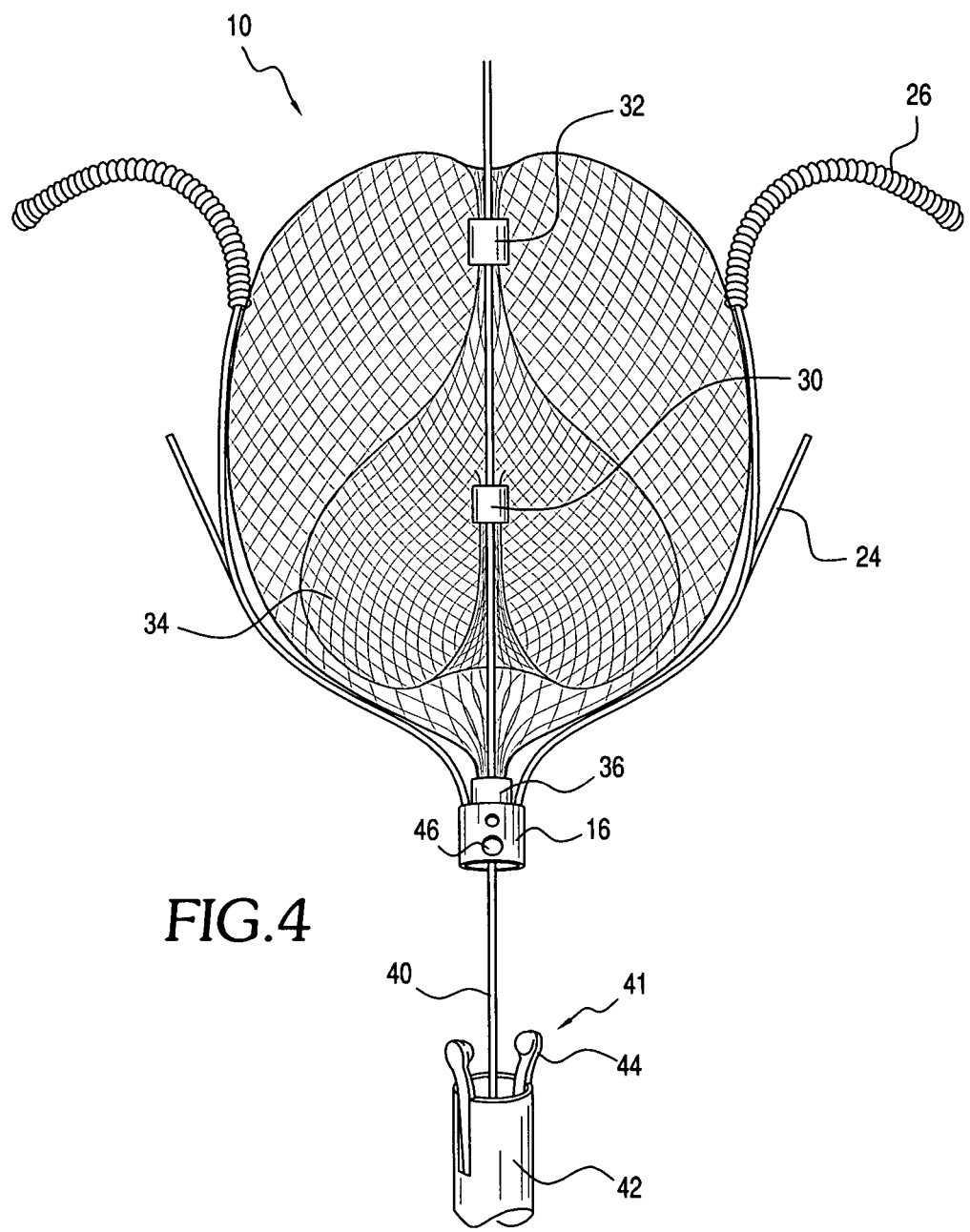
FIG. 4 illustrates a preferred embolic filtering device and delivery mechanism.

The embolic filtering device 10 is particular useful in preventing the passage of emboli between an venous blood pool and an arterial blood pool. For purposes of exemplary illustration, the method of the invention is herein exemplified through discussion of a method of treating a patent foramen ovale (PFO). However, it should be recognized that the invention can be used to prevent the passage of emboli between any septal defect and/or arterial venous blood pool and arterial blood pool. To deliver the embolic filtering device 10 of the patent foramen ovale, embolic filtering device 10 is loaded into a delivery system 41 comprising a catheter 42, exemplified in FIG. 4. In a preferred embodiment, the embolic filtering device 10 is loaded onto a guide wire 40 by inserting the guide wire through the lumens of first base 16, the lumens of fasteners 30, 32, and 36, if employing a frame 12 with second base 18, the lumen of second base 18, A pair of forceps 44, as exemplified in FIG. 4, or other grasping device, is used to grasp embolic filtering device 10. In a preferred embodiment, first base 16 has a recess 46 for receiving forceps 44, such that forceps 44 are positioned within recess 46 to more securely grasp embolic filtering device 10, and to deter embolic filtering device 10 from detaching from forceps 44. With embolic filtering device 10 secured by forceps 44 embolic filtering device 10 is pulled into catheter 42. As embolic filtering device 10 is pulled into catheter 42, the force of the catheter walls against first base 16 of frame 12 will force side walls 20 and 22, and left anchors 26 and right anchors 24 inward toward one another. Embolic filtering device 10 will gradually collapse as it is pulled into catheter 42.

Figure 5C:
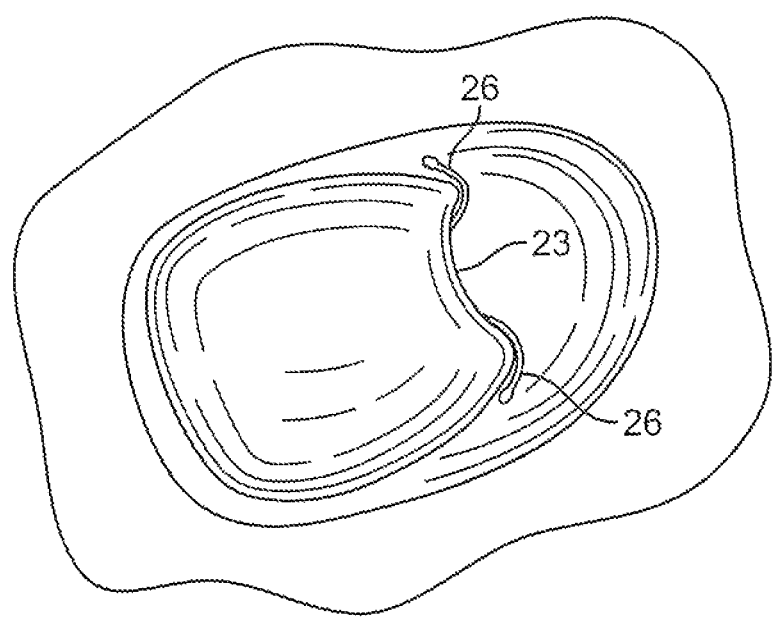

Using catheter 42, embolic filtering device 10 is delivered to the patent foramen ovale, or other passage between a venous blood pool or arterial blood pool, to be treated. In particular, the distal end of catheter 42 is extended through the patent foramen ovale from the right atrial side to the left atrial side. With the distal end of catheter 42 positioned in the left atrium adjacent to the patent foramen ovale, forceps 44 are used to withdraw embolic filtering device 10 from catheter 42. As embolic filtering device 10 is withdrawn, embolic filtering device 10 will gradually expand from its collapsed position and into its memorized shape and/or in conformance to the shape and dimension of the patent foramen ovale being treated. With the distal end of catheter 42 positioned in the left atrium, adjacent to the patent foramen ovale, embolic filtering device 10 is withdrawn from catheter 42, while catheter 42 is slowly pulled back through the patent foramen ovale in the direction of the right atrium. Left anchors 26 are withdrawn first, and as catheter 42 is pulled back, left anchors 26 are caused to securely engage the walls defining the patent foramen ovale, preferably, the tissue defining the perimeter of the left-atrial opening 23 of the patent foramen ovale, as shown in FIG. 5C. As catheter 42 is pulled back further, the engagement of left anchors 20 onto the tissue defining the perimeter of left-atrial opening 23 of arms 20 and 22 will prevent embolic filter device 10 from being pulled through the patent foramen ovale, and embolic filter 14 will emerge preferably within the patent foramen ovale, and will gradually expand apart from one another in returning to the shape memorized orientation. As arms 20 and 22 expand apart from one another, pressure will be exerted onto the tissue defining the lumen of the patent foramen ovale, thereby acting as a tissue distension device. The tissue defining the patent foramen ovale will naturally press inward against mesh 14, in effect squeezing the device within the patent foramen ovale. As catheter 42 is pulled back yet further, right anchors 24 will emerge and, as they expand to their memorized shape, will also forcibly engage, for example, the walls defining the patent foramen ovale, or the perimeter of the tissue defining right atrial opening 31 of the patent foramen ovale. If using the embolic filter device illustrated in FIG. 5A, for example, right anchors 24 will engage the tissue defining the outside perimeter defining the right-atrial opening 31 of the patent-foramen ovale, as illustrated, in FIG. 5B. In its memorized, shape, embolic filter 14 should be sized to engage the walls defining the patent foramen ovale with sufficient force to prevent emboli from passing between the exterior of the embolic filter 14 and the walls of defining the patent foramen ovale. Further, the force created from blood flowing from the right atrium to the left atrium against right anchors 24 facilitates the securing, of right anchors 24, and helps prevent embolic filtering, device 10 from becoming dislodged from its intended position.

It will be recognized by those of ordinary skill, that the device can further be secured in place by adhesives, sutures, hooks, barbs, or other such means. To enhance recovery subsequent to implanting embolic filtering device 10 frame 12 and/or mesh 14 can be coated with known drugs suitable for that purpose. Non-pharmacological methods can also be used to promote healing, including ultrasound, radiofrequency, radiation, mechanical vibration, or any other known non-pharmacological healing method.

Prior to disengaging embolic filtering device 10 from forceps 44 and removing catheter 42 from the subject, known radiological techniques can be employed to insure that embolic filtering device 10 is properly positioned and secured within the patent foramen ovale. If the position of embolic filtering device 10 needs to be altered, forceps 44, while still secured to embolic filtering device 10, can be used to reposition embolic filtering device 10; otherwise, forceps 44 are disengaged from embolic filtering device 10, and forceps 44, catheter 42, and guide wire 40 are withdrawn. Should embolic filter device 10 later become disengaged, disoriented, damaged or otherwise need to be removed, forceps 44 can be used to easily reposition or recover embolic filter device 10, as necessary. To facilitate the ease by which embolic filter device 10 is repositioned or recovered, base 16 is preferably coated with a suitable material to deter tissue from covering recess 46.

From the moment that embolic filtering device 10 is inserted, emboli are effectively filtered by embolic filtering device 10. Since blood travels from the direction of the right atrium to the left atrium, the portion of embolic filter 14 having a higher density of mesh, e.g., lobes 29 and/or interior embolic filter portion 34, are positioned on the right atria side to decrease the chances that emboli will penetrate into the left atrium. The design of embolic filtering device 10, however, is such that if emboli pass through the right side of embolic filter 14, there is still a significant chance that the portion of embolic filter 14 positioned on the left atrial side will prevent the emboli from passing into the left atrium.

Thus, unlike known devices for treating patent foramen ovale or atrial septal defects, for example, it is not necessary for thrombi to collect on the embolic filtering device 10 before the passage of emboli are effectively deterred. However, if total occlusion of the passage is desired, embolic filtering device 10 the embolic filter 14 can be treated with materials to promote thrombosis, tissue in-growth, or adhesions. Embolic filter 14 can also be treated with anticoagulants to discourage blood clot formation on the device 10.

The primary function of frame 12 is to facilitate the delivery, positioning and securing of the embolic filter 14 within and/or adjacent to a passage between a venous blood pool and an arterial blood pool. It should be appreciated, however, that embolic filter 14 can be employed by itself, without frame 12, by securing embolic filter 14 by other means, e.g. sutures, hooks, etc., to deter the passage of emboli through a passage between a venous blood pool and an arterial blood pool. Further, embolic filter 14 can be of virtually any shape, spherical, round, oval or flat, so long as it retains its ability to filter emboli.

In another aspect of the invention, as exemplified in FIGS. 6A and 6B, provided is an embolic filter device 110 composed of a mesh 112 and a frame 114, to which mesh 112 is attached. Mesh 112 can be composed of any suitable material, including fabric, metal (e.g. shape memory metal or non-shape memory metal), or polymer, and can be of any shape (e.g., round, oval, or flat) or size suitable for the opening to be treated. Frame 114 can also be composed of any suitable material. For example, frame 114 can be composed of fabric, if rigidity is not required to support the opening to be treated. Alternatively, frame 114 can be composed of plastic, metal or the like, so as to act as a stent to give support to the orifice through which the passage of embolic is to be deterred. Depending on the particular use, mesh 112 and/or frame 114 can be absorbable or non-absorbable. To deter the passage of emboli from a passage between a venous blood pool and an arterial blood pool, embolic filtering device 110 is preferably used to block the passage between a venous blood pool and an arterial blood pool. Using the example of a patent foramen ovale, embolic filtering device 100 can be attached to tissue adjacent to the patent foramen ovale by for example, sutures, barbs, hooks, glue, or any other suitable attaching means 116 to, in effect, create a screen covering the right atrial and/or left atrial openings, and/or within the lumen of the patent foramen ovale. The attaching means 116 are preferably on frame 114, but can be placed at any suitable location on embolic tiller device 110. Once in place, embolic filtering device 110 effectively deters the passage of emboli from the right atrium to the left atrium via the patent foramen ovale. Embolic filter device may be delivered either percutaneously, surgically, or via a catheter, depending on the area to be treated.

The invention has been described through a preferred embodiment. However, those of ordinary skill will recognize that various modifications can be made without departing from the scope of the invention as defined by the claims.

What is claimed is:

1. A method for occluding a lumen of a septal defect of a heart comprising:
    delivering a treatment device into the defect lumen in a collapsed configuration, wherein the device comprises a frame disposed in a frame plane, occlusion promoting material supported by the frame, a first anchor extending from a first end of the device, and a second anchor extending from a second end of the device;
    moving the first anchor to engage first side of a tissue wall defining the defect;
    expanding the frame in the frame plane within the defect lumen, distending septal defect lumen tissue outward in the frame plane and pressing septal defect lumen tissue in contact with occlusion promoting material; and
    moving the second anchor to engage a second side of the tissue wall defining the defect.

2. The method of claim 1 wherein the septal defect is a patent foramen ovale.

3. The method of claim 1 wherein the occlusion promoting material extends out of the frame plane.

4. The method of claim 1 wherein the occlusion promoting material comprises foam.

5. The method of claim 1 wherein the occlusion promoting material comprises mesh.

6. The method of claim 5 wherein the mesh comprises a plurality of Nitinol wires.

7. The method of claim 1 wherein the occlusion promoting material comprises collagen, fabric, adhesive or polymer.

8. The method of claim 1 wherein no portion of the frame supporting the occlusion promoting material extends out of the frame plane.

9. The method of claim 1 wherein the treatment device further comprises a third anchor extending from the first end of the device, the step of moving the first anchor comprising expanding the first and third anchors away from each other to engage the first outer side of the tissue wall defining the defect.

10. The method of claim 9 wherein the step of expanding the first and third anchors comprises moving the first and third anchors in the frame plane.

11. The method of claim 1 wherein the treatment device further comprises a third anchor extending from the second end of the device, the step of moving the second anchor comprising expanding the second and third anchors away from each other to engage the second side of the tissue wall defining the defect.

12. The method of claim 11 wherein the step of expanding the second and third anchors comprises moving the second and third anchors in the frame plane.

\* \* \* \* \*